US010238425B2

(12) United States Patent
Clifford et al.

(10) Patent No.: US 10,238,425 B2
(45) Date of Patent: Mar. 26, 2019

(54) IMPLANTABLE ASSEMBLY FOR A KNEE JOINT AND METHOD FOR MOUNTING AN IMPLANTABLE ASSEMBLY FOR A KNEE JOINT

(71) Applicant: MOXIMED, INC., Hayward, CA (US)

(72) Inventors: Anton G. Clifford, Mountain View, CA (US); Nathaniel Skinner, Indianapolis, IN (US)

(73) Assignee: MOXIMED, INC., Fremont, CA (US)

( * ) Notice: Subject to any disclaimer, the term of this patent is extended or adjusted under 35 U.S.C. 154(b) by 281 days.

(21) Appl. No.: 15/290,497

(22) Filed: Oct. 11, 2016

(65) Prior Publication Data

US 2017/0112537 A1     Apr. 27, 2017

Related U.S. Application Data

(63) Continuation of application No. PCT/US2015/025300, filed on Apr. 10, 2015.

(60) Provisional application No. 61/978,238, filed on Apr. 11, 2014.

(51) Int. Cl.
*A61B 17/56* (2006.01)
(52) U.S. Cl.
CPC ........ *A61B 17/56* (2013.01); *A61B 2017/564* (2013.01); *A61B 2017/567* (2013.01)
(58) Field of Classification Search
CPC ............................. A61B 17/56; A61B 17/567
See application file for complete search history.

(56) References Cited

U.S. PATENT DOCUMENTS

| 2004/0180072 A1 | 9/2004 | Tunc et al. |
| 2006/0064169 A1 | 3/2006 | Ferree |
| 2007/0043356 A1 | 2/2007 | Timm et al. |
| 2008/0275563 A1* | 11/2008 | Makower ............... A61B 17/68 623/20.21 |
| 2012/0022655 A1 | 1/2012 | Clifford |
| 2013/0325122 A1 | 12/2013 | Gabriel et al. |

FOREIGN PATENT DOCUMENTS

| WO | WO2011/153026 A2 | 12/2011 |
| WO | WO2014/138595 A1 | 9/2014 |

OTHER PUBLICATIONS

International Search Report for PCT Patent App. No. PCT/US2015/025300 (dated Jul. 27, 2015).
Written Opinion for PCT Patent App. No. PCT/US2015/025300 (dated Jul. 27, 2015).
Extended European Search Report for European Patent App. No. 15776845.8 dated Dec. 5, 2017.

* cited by examiner

*Primary Examiner* — Christian Sevilla
(74) *Attorney, Agent, or Firm* — Cermak Nakajima & McGowan LLP; Adam J. Cermak (57) ABSTRACT

An implantable assembly (21) for a knee joint includes a force absorber assembly (33) connected to a first attachment structure (25) for a tibia and a second attachment structure (29) for a femur. The absorber assembly includes a cylinder body (47) connected to the first attachment structure and a piston (41) connected to the second attachment structure. The piston includes a first portion (39) connected to the second attachment structure and a second portion receivable in a cylinder body opening (43) of the cylinder body, the second portion of the piston being of greater flexibility than the first portion of the piston.

29 Claims, 7 Drawing Sheets

IMPLANTABLE ASSEMBLY FOR A KNEE JOINT AND METHOD FOR MOUNTING AN IMPLANTABLE ASSEMBLY FOR A KNEE JOINT

BACKGROUND AND SUMMARY

The present invention relates generally to implantable assemblies for knee joints and to methods for mounting such implantable assemblies.

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced. Arthroplasty as a general term, is an orthopaedic procedure which surgically alters the natural joint in some way. This includes procedures in which the arthritic or dysfunctional joint surface is replaced with something else, procedures which are undertaken to reshape or realigning the joint by osteotomy or some other procedure. As with joint replacement, these other arthroplasty procedures are also characterized by relatively long recovery times and their highly invasive procedures. A previously popular form of arthroplasty was interpositional arthroplasty in which the joint was surgically altered by insertion of some other tissue like skin, muscle or tendon within the articular space to keep inflammatory surfaces apart. Another previously done arthroplasty was excisional arthroplasty in which articular surfaces were removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity. When it is successful, arthroplasty results in new joint surfaces which serve the same function in the joint as did the surfaces that were removed. Any chondrocytes (cells that control the creation and maintenance of articular joint surfaces), however, are either removed as part of the arthroplasty, or left to contend with the resulting joint anatomy. Because of this, none of these currently available therapies are chondro-protective.

A widely-applied type of osteotomy is one in which bones are surgically cut to improve alignment. A misalignment due to injury or disease in a joint relative to the direction of load can result in an imbalance of forces and pain in the affected joint. The goal of osteotomy is to surgically re-align the bones at a joint and thereby relieve pain by equalizing forces across the joint. This can also increase the lifespan of the joint. When addressing osteoarthritis in the knee joint, this procedure involves surgical re-alignment of the joint by cutting and reattaching part of one of the bones at the knee to change the joint alignment, and this procedure is often used in younger, more active or heavier patients. Most often, high tibial osteotomy (HTO) (the surgical re-alignment of the upper end of the shin bone (tibia) to address knee malalignment) is the osteotomy procedure done to address osteoarthritis and it often results in a decrease in pain and improved function. However, HTO does not address ligamentous instability—only mechanical alignment. HTO is associated with good early results, but results deteriorate over time.

Other approaches to treating osteoarthritis involve an analysis of loads which exist at a joint. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Finally, if the load rises too high, then abrupt failure of bone, cartilage and other tissues can result. Accordingly, it has been concluded that the treatment of osteoarthritis and other bone and cartilage conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain but have ultimately been unsuccessful due to lack of patient compliance or the inability of the devices to facilitate and support the natural motion and function of the diseased joint. The loads acting at any given joint and the motions of the bones at that joint are unique to the body that the joint is a part of. For this reason, any proposed treatment based on those loads and motions must account for this variability to be universally successful. The mechanical approaches to treating osteoarthritis have not taken this into account and have consequently had limited success.

Prior approaches to treating osteoarthritis have also failed to account for all of the basic functions of the various structures of a joint in combination with its unique movement. In addition to addressing the loads and motions at a joint, an ultimately successful approach must also acknowledge the dampening and energy absorption functions of the anatomy, and be implantable via a minimally invasive technique. Prior devices designed to reduce the load transferred by the natural joint typically incorporate relatively rigid constructs that are incompressible. Mechanical energy (E) is the action of a force (F) through a distance (s) (i.e., $E=F \times S$). Device constructs which are relatively rigid do not allow substantial energy storage as the forces acting on them do not produce substantial deformations—do not act through substantial distances—within them. For these relatively rigid constructs, energy is transferred rather than stored or absorbed relative to a joint. By contrast, the natural joint is a construct comprised of elements of different compliance characteristics such as bone, cartilage, synovial fluid, muscles, tendons, ligaments, etc. as described above. These dynamic elements include relatively compliant ones (ligaments, tendons, fluid, cartilage) which allow for substantial energy absorption and storage, and relatively stiffer ones (bone) that allow for efficient energy transfer. The cartilage in a joint compresses under applied force and the resultant force displacement product represents the energy absorbed by cartilage. The fluid content of cartilage also acts to stiffen its response to load applied quickly and dampen its response to loads applied slowly. In this way, cartilage acts to absorb and store, as well as to dissipate energy.

With the foregoing applications in mind, it has been found to be necessary to develop effective structures for mounting to body anatomy. Such structures should conform to body anatomy and cooperate with body anatomy to achieve desired load reduction, energy absorption, energy storage, and energy transfer. These structures should include mounting means for attachment of complementary structures across articulating joints.

For these implant structures to function optimally, they must not cause an adverse disturbance to joint motion. Therefore, what is needed is an approach which addresses both joint movement and varying loads as well as complements underlying or adjacent anatomy. It is also desirable that they occupy a minimal footprint and are simple to position.

According to an aspect of the present invention, an implantable assembly for a knee joint comprises a first attachment structure configured to be attached to a first member of the knee joint, a second attachment structure configured to be attached to a second member of the knee joint, and a force absorber assembly connected to the first attachment structure and the second attachment structure, the absorber assembly including a cylinder body connected to the first attachment structure and a piston connected to the second attachment structure, the piston including a first portion connected to the second attachment structure and a second portion receivable in a cylinder body opening of the cylinder body, the second portion of the piston being of greater flexibility than the first portion of the piston.

According to another aspect of the present invention, a method for mounting an implantable assembly for a knee joint comprises fixing a first attachment structure to a tibia via a pair of screws, attaching a first end of a laterally and longitudinally flexible force absorber assembly to a first connection point of the first attachment structure, drilling a first hole in a femur, inserting a post of a second attachment structure into the first hole, positioning a remaining portion of the second attachment structure on the post so that the remaining portion of the second attachment structure is rotatable about the post, rotating the remaining portion of the second attachment structure about the post to align a second connection point of the second attachment member with a second end of the force absorber assembly, and after rotating the remaining portion of the second attachment structure about the post, fixing the remaining portion of the second attachment structure to the femur via a screw.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1A:
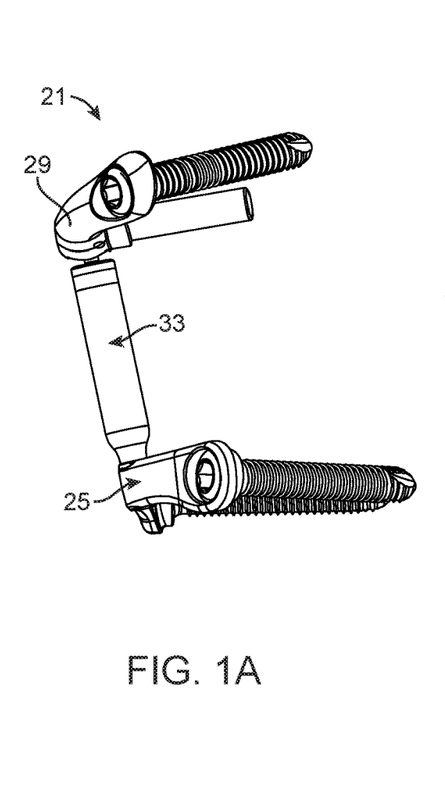
FIGS. 1A and 1B are front and side perspective views of the implantable assembly according to an aspect of the present invention.
Figure 1B:
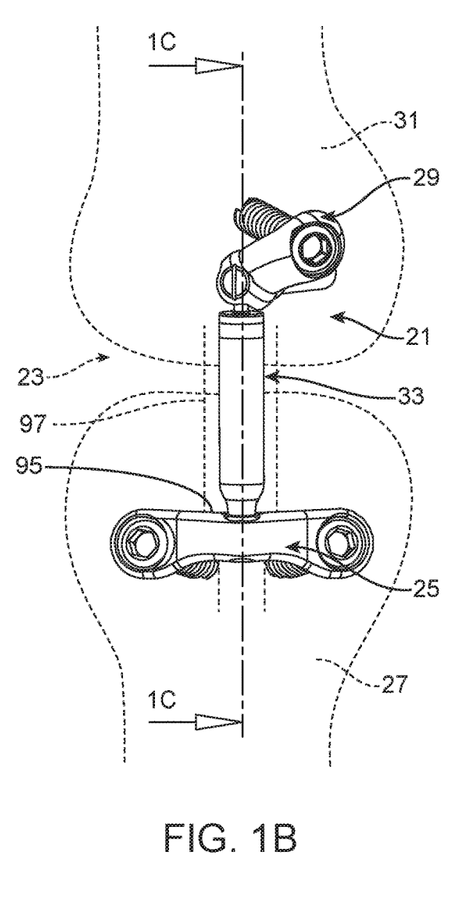
Figure 1C:
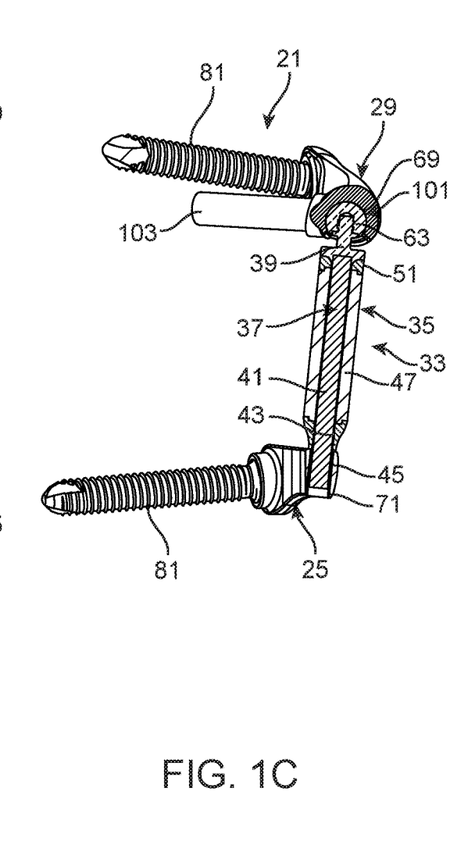
FIG. 1C is a partially cross-sectional view of the implantable assembly of FIG. 1B taken at section 1C-1C.
Figure 2A:
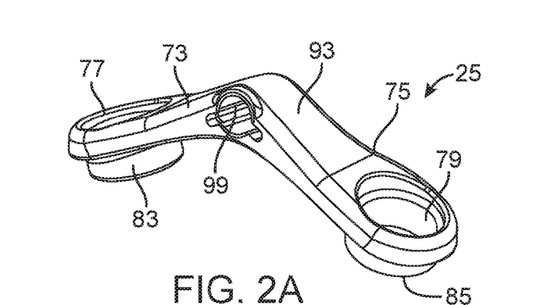
FIGS. 2A-2D are top perspective, top, side, and bottom views, respectively, of a first attachment structure according to an aspect of the present invention.
Figure 2B:
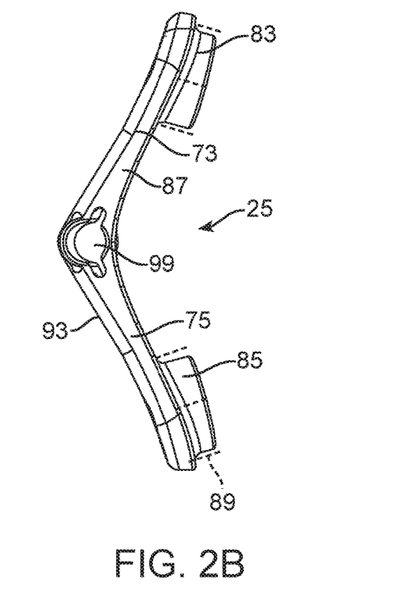
Figure 2C:
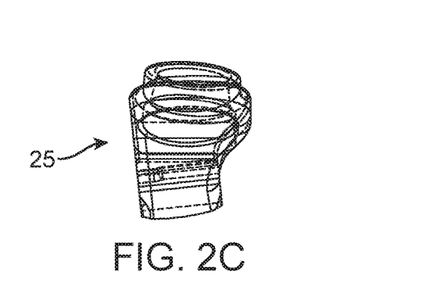
Figure 2D:
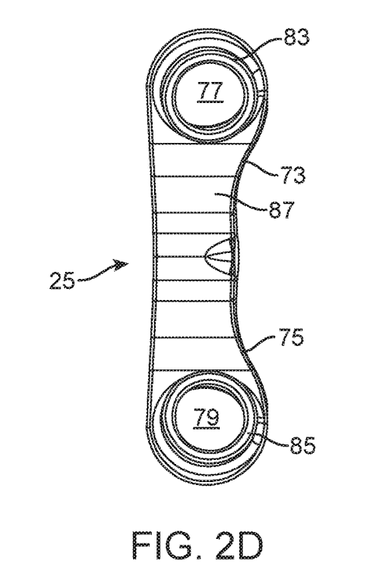
Figure 3A:
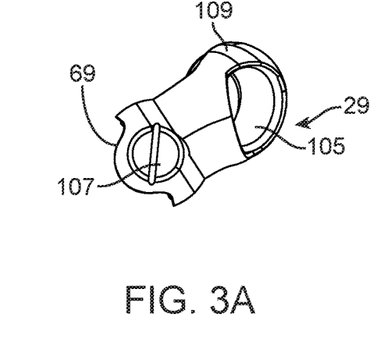
FIGS. 3A-3C are front, side, and bottom views, respectively, of a second attachment structure according to an aspect of the present invention.
Figure 3B:
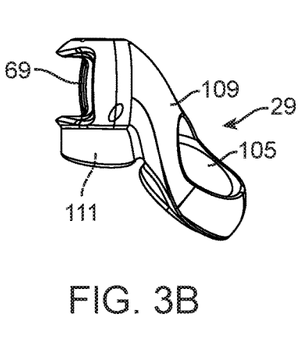
Figure 3C:
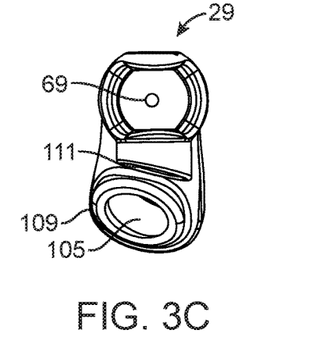
Figure 4:
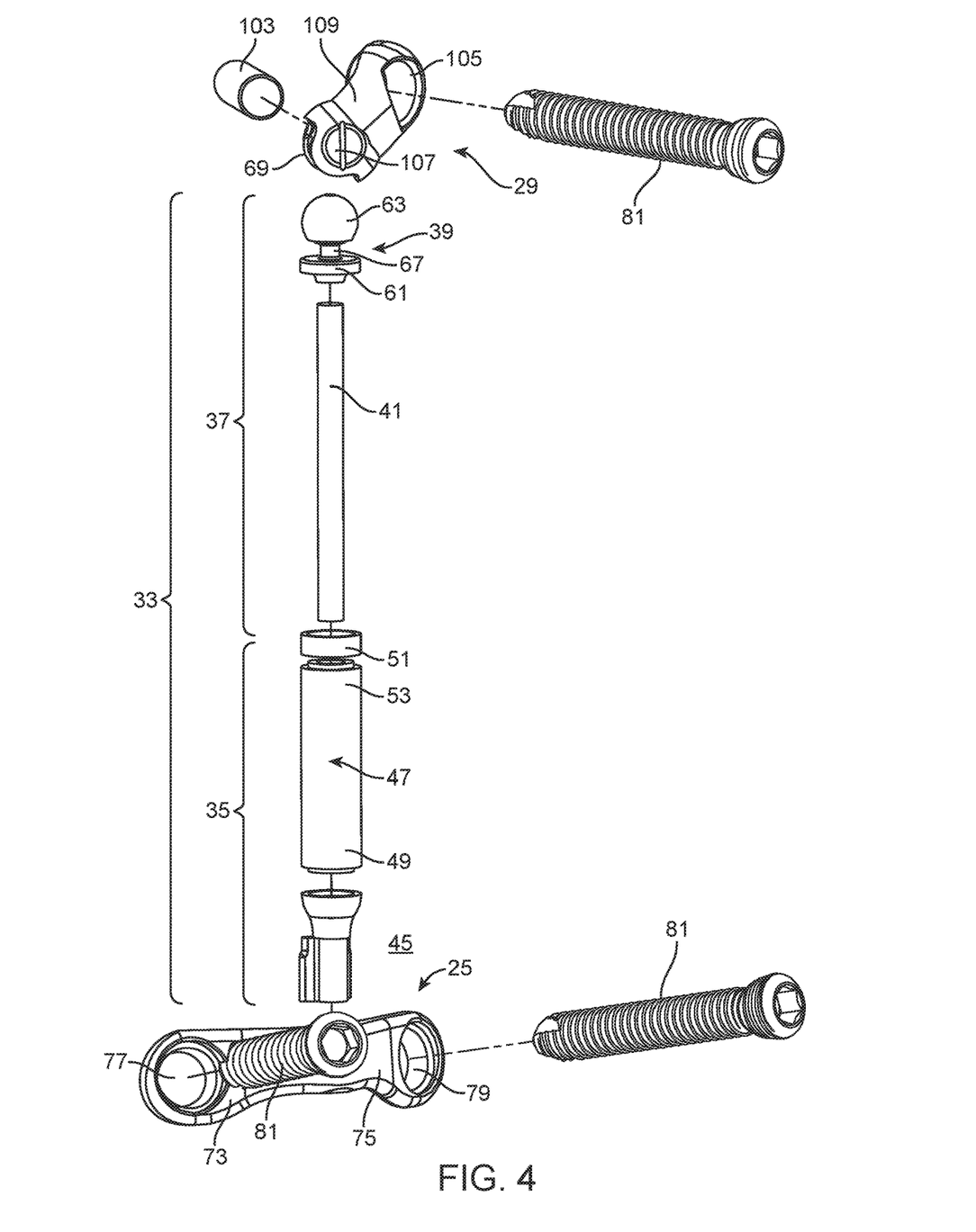
FIG. 4 is an exploded, front perspective view of the implantable assembly according to an aspect of the present invention.
Figure 5A:
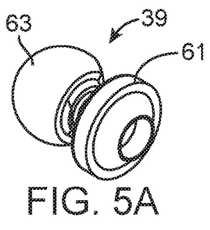
FIGS. 5A-5D are bottom perspective, side, top perspective, and bottom views, respectively, of a first portion of a piston according to an aspect of the present invention.
Figure 5B:
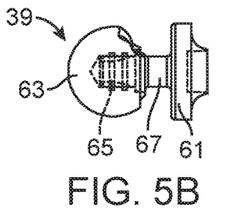
Figure 5C:
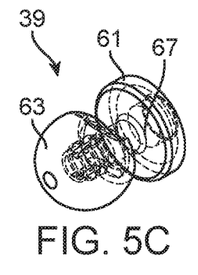
Figure 5D:
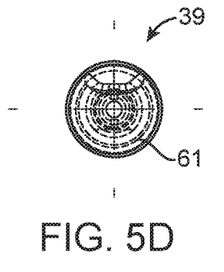

FIG. 1A-1C show an implantable assembly 21 according to an aspect of the present invention for a knee joint 23. The implantable assembly 21 includes a first attachment structure 25 (FIGS. 2A-2D) configured to be attached to a first member 27 (shown in phantom in FIG. 1B as the tibia) of the knee joint 23, a second attachment structure 29 (FIGS. 3A-3C) configured to be attached to a second member 31 (shown in phantom in FIG. 1B as the femur) of the knee joint, and a force absorber assembly 33 (seen in an exploded view in FIG. 4) connected to the first attachment structure and the second attachment structure.

Figure 6A:
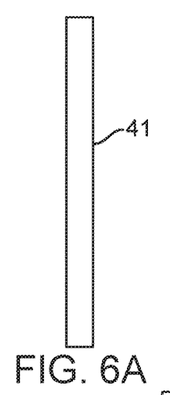
FIGS. 6A-6B are side and top views, respectively, of a second portion of a piston according to an aspect of the present invention.
Figure 6B:
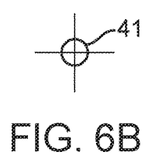
Figure 7A:
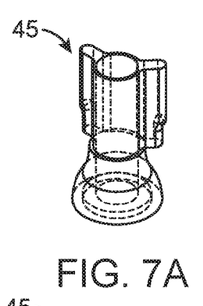
FIGS. 7A-7D are top perspective, front, side, and top views, respectively, of a first portion of a cylinder body according to an aspect of the present invention.
Figure 7B:
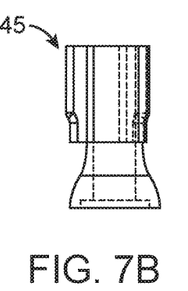
Figure 7C:
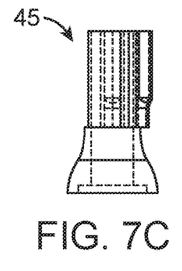
Figure 7D:
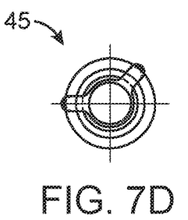

The force absorber assembly 33 includes a cylinder body 35 connected to the first attachment structure 25 and a piston 37 connected to the second attachment structure 29. The piston 37 includes a first portion 39 (FIGS. 5A-5D) connected to the second attachment structure 29 and a second portion 41 (FIGS. 6A-6B) receivable in a cylinder opening 43 of the cylinder body 35. The second portion 41 of the piston 37 is of greater flexibility than the first portion 39 of the piston and, more particularly, is ordinarily laterally bendable and may also be axially compressible. By way of example and not of limitation, materials suitable for the second portion 41 include HDPE, LDPE, NiTi wire, braided wire, and PCU-covered wire. The second portion 41 of the piston 37 is usually at least sufficiently flexible to permit the second portion of the piston to be received in the cylinder opening 43 even though a desired alignment of the second attachment structure 29 relative to the cylinder body 35 is absent and a portion of the second portion of the piston outside of the cylinder opening 43 is bent. The piston's flexibility, as expressed as bending stiffness in $N/mm^2$, can be designed to be greater than that of the cylinder, to reduce buckling of the cylinder. Alternatively, the piston's flexibility can be equal to that of the cylinder, to provide even bending behavior of the assembly. Further alternatively, the piston's flexibility can be less than that of the cylinder, to be the primary bending element. Preferably and advantageously, the piston's flexibility is designed to be ±25% of the flexibility of the flexibility of the cylinder. The first portion 39 of the piston 37 is typically formed of a suitable, relatively inflexible and incompressible, bio-compatible material such as titanium or PEEK, although other materials, such as stainless steel, CoCr, and MP35N, can optionally be used. When the second portion 41 of the piston 37 is received in the cylinder opening 43, the piston and the cylinder body 35 are ordinarily axially rotatable relative to each other.

Figure 8A:
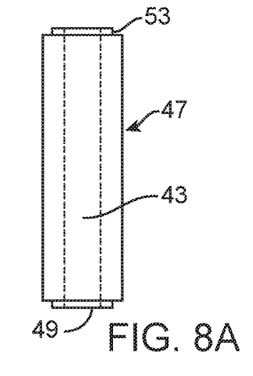
FIGS. 8A-8B are side and top views, respectively, of a second portion of a cylinder body according to an aspect of the present invention.
Figure 8B:
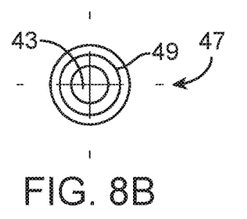

The cylinder body 35 can include a first portion 45 (FIGS. 7A-7D) connected to the first attachment structure 25 and a second portion 47 (FIGS. 8A-8B) including at least part of the cylinder opening 43 in which the second portion 41 of the piston 37 is receivable. The second portion 47 of the cylinder body 35 is ordinarily of greater flexibility than the first portion 39 of the piston 37, as expressed as bending stiffness in $N/mm^2$. The second portion 47 of the cylinder body 35 can be axially compressible and may be laterally bendable, as well. The second portion 47 of the cylinder body 35 is ordinarily of greater flexibility than the first portion 45 of the cylinder body. The first portion 45 of the cylinder body 35 is typically formed of a suitable, relatively inflexible and incompressible, bio-compatible material such as, but not limited to, PCU, silicone, and NiTi. The first portion 45 of the cylinder body 35 is ordinarily non-rotatably attached to the first attachment structure 25. The first attachment structure 25 ordinarily includes an opening 99 in which an end of the first portion 45 of the cylinder body 35 is locked so that it cannot be removed from the opening.

Figure 9A:
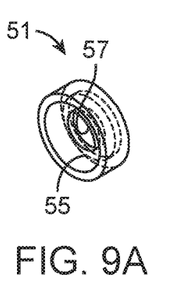
FIGS. 9A-9C are bottom perspective, side, and top views, respectively, of a third portion of a cylinder body according to an aspect of the present invention.
Figure 9B:
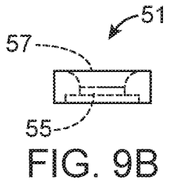
Figure 9C:
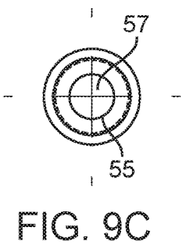

The first portion 45 of the cylinder body 35 is disposed at a first end 49 of the second portion 47 of the cylinder body, and the cylinder body can include a third portion 51 (FIGS. 9A-9C) disposed at a second, opposite end 53 of the second portion of the cylinder body. The third portion 51 of the cylinder body 35 can be in the form of a cap so that the end 53 of the second portion 47 of the cylinder body can be received in a recess 55 in the third portion of the cylinder body. The second portion 47 of the cylinder body 35 is ordinarily of greater flexibility than the third portion 51 of the cylinder body. The second portion 47 of the piston 37 is adapted to extend through a first portion of the cylinder opening 43 in the form of an opening 57 in the third portion 51 of the cylinder body 35 into a second portion of the cylinder opening in the form of an opening 59 in the second portion 47 of the cylinder body.

The first portion 39 of the piston 37 can include a flange portion 61 having a larger diameter than the second portion 41 of the piston and than the cylinder opening 43. The second portion 41 of the piston 37 is ordinarily of greater flexibility than the flange portion 61, and the flange portion is ordinarily of a suitable, relatively inflexible and incompressible, bio-compatible material such as stainless steel, NiTi, CoCr, Ti, and MP35N. The first portion 39 of the piston 37 ordinarily further includes a ball 63 attached to the flange portion 61. As seen, for example, in FIG. 5B, the ball 63 can include an internally threaded portion 65 and a screw 67 attached to or formed with the flange portion can mate with the internally threaded portion. The second portion 39 of the piston 37 is ordinarily of greater flexibility than the ball 63, and the ball is ordinarily of a suitable, relatively inflexible and incompressible, bio-compatible material such as, but not limited to, CoCr, ceramic, PEEK, and fiber-reinforced PEEK.

The second attachment structure 29 ordinarily includes a socket 69 in which the ball 63 is received. The force absorber assembly 33 is pivotable relative to the second attachment 29 structure via the ball 63 and socket 69.

Figure 10:
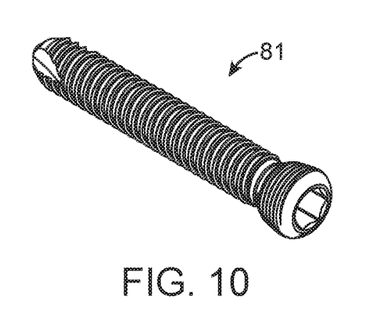
FIG. 10 is a perspective view of a screw according to an aspect of the present invention.

The first attachment structure 25 includes a connection point 71 for the cylinder body 35 and a pair of legs 73 and 75 disposed on opposite sides of the connection point. Each leg includes an opening 77 and 79, respectively, for receiving a screw 81 (FIG. 10). Each leg 77 and 79 includes a respective boss 83 and 85 protruding from a rear surface 87 of the first attachment structure, the opening extending through the boss. As seen in phantom in FIG. 2B. each boss 83 and 85 can include an external surface including one or more axially extending ridges 89 that can facilitate securing the first attachment structure 25 to a first member 27. Each opening 77 and 79 is countersunk in a respective leg 77 and 79 to receive an enlarged head 91 portion of the screw 81 beneath an outer surface 93 of the respective leg. In this way, the bosses 83 and 85 and openings 77 and 79 permit the screws 81 to lock the first attachment structure 25 relative to the first member 27 without adding to the profile of the implantable assembly.

The pair of legs 73 and 75 define an obtuse angle relative to each other and ordinarily define, with a tibia 27 to which they are mounted, a space 95 of sufficient size to span a medial collateral ligament 97 (MCL) (shown in phantom in FIG. 1B). The space 95 is ordinarily of sufficient size to permit MCL 97 movement in the space.

The connection point 71 on the first attachment structure 25 for the cylinder body 35 ordinarily includes an opening 99 in the first attachment structure in which the first portion 45 of the cylinder body 35 is locked (meaning fixed or secured in any of a number of suitable fashions) so that it cannot be removed from the opening. The opening 99 of the connection point 71 for the cylinder body 35 includes an axis that is substantially perpendicular to axes of the screw receiving openings 77 and 79. This arrangement can facilitate providing a minimal footprint for the first attachment structure 25. It will be seen from, e.g., FIGS. 1A and 2B, that the axes of the screw receiving openings 77 and 79 ordinarily define an acute angle, and an axis of the opening 99 is not perfectly perpendicular to and typically defines an obtuse angle with axes of the screw receiving openings.

The second attachment structure 29 includes a connection point 101 for the piston 37, a post 103, and an opening 105 for receiving a screw 81. The screw 81 is ordinarily of the same type as the screws that secure the first attachment structure 25. The connection point 101 for the piston 37 ordinarily includes the socket 69 in which the ball 63 on the piston is received. The force absorber assembly 33 is ordinarily pivotable relative to the second attachment structure 29 via the ball 63 and socket 69. A longitudinal axis of the post 103 extends through a center of the ball 63 and socket 69. The post 103 may be made of suitable, relatively inflexible and incompressible, bio-compatible material such as, but not limited to, titanium, PEEK, stainless steel, and CoCr.

The socket 69 can include alignment indicia 107 arranged to align with a longitudinal axis of force absorber assembly 33. The second attachment structure 29 ordinarily includes a leg 109 extending from the connection point 101 for the piston 37. The opening 105 for receiving the screw 81 can be disposed in the leg 109. The second attachment structure 29 typically includes an opening 111 in which the post 103 is received. A longitudinal axis of the opening 111 for the post 103 ordinarily defines an acute angle with a longitudinal axis of the opening 105 for the screw, and the post is ordinarily pivotable in the opening 111. The remaining portion of the second attachment structure 29 (i.e., other than the post 103) is typically formed of a suitable, relatively inflexible and incompressible, bio-compatible material such as, but not limited to, PEEK, Ti, stainless steel, and CoCr.

The second attachment structure 29 facilitates a simple procedure and requires a minimal footprint for attachment to the second member 31 (a femur). After locating the femoral epicondyle 201, a hole 203 can be drilled in the femur 31 at a location distal to the femoral epicondyle (in a presently preferred design, the hole is drilled 3 mm distal to the femoral epicondyle). The post 103 is inserted into the hole 203 and is also inserted in the opening 111 of the second attachment member 29. The socket 69 and leg 109 of the second attachment member 29 can then be pivoted around the post 103 until the alignment indicia 107 aligns with the longitudinal axis of the force absorber assembly 33. A hole 217 can then be drilled in the femur 31 for the screw 81 through the opening 105 in the leg 109. The alignment indicia 107 can have a variety of suitable forms but is illustrated in, e.g., FIG. 1B as an elongated feature (groove) on the second connection point 101, more particularly, on the socket 69.

Figure 11A:
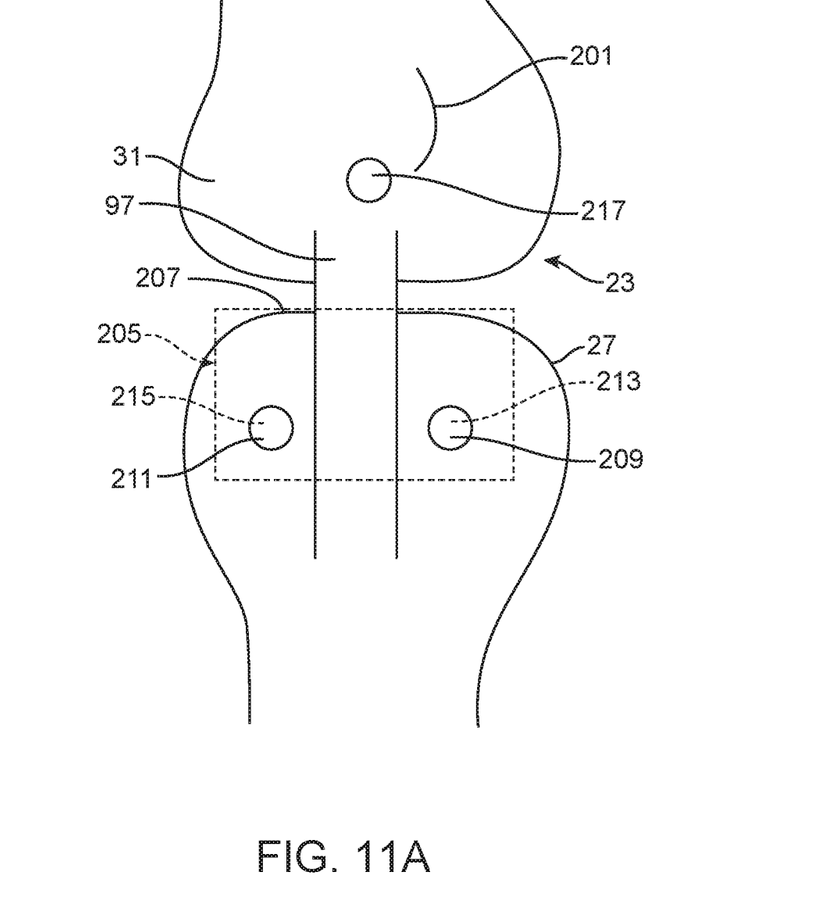
FIGS. 11A-11C show steps in a method for mounting an implantable assembly for a knee joint according to an aspect of the present invention.
Figure 11B:
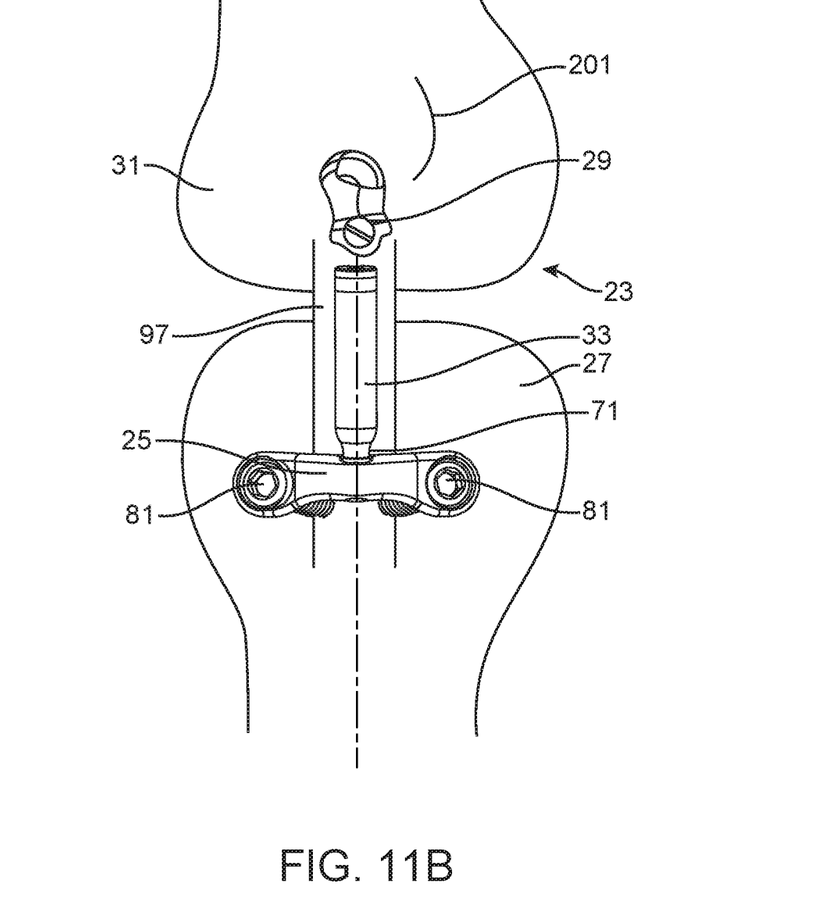
Figure 11C:
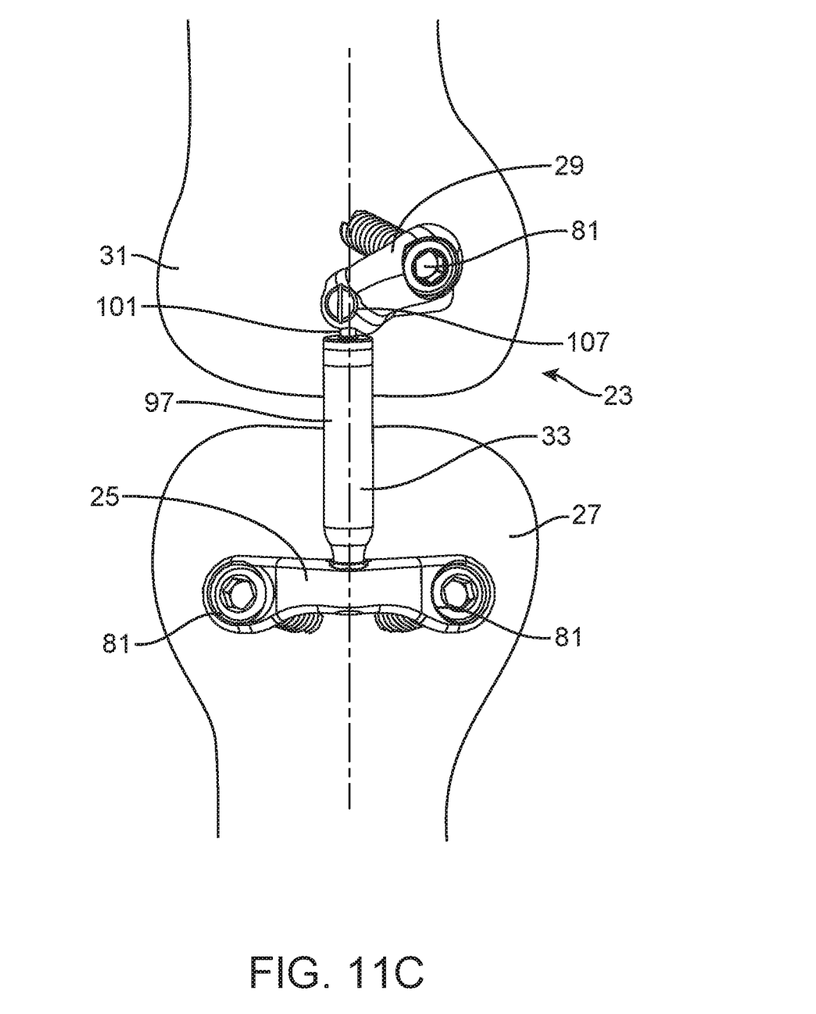

A method for mounting the implantable assembly 21 relative to a knee joint 23 is shown in FIGS. 11A-11C. In the method, as seen in FIG. 11A, the femoral epicondyle 201 is located and a hole 203 can be drilled in the femur 31 at a location distal to the femoral epicondyle. In a presently preferred design, the hole 203 is drilled 3 mm distal to the femoral epicondyle. The post 103 is inserted into the hole 203.

A template 205 can be provided to identify a position for drilling (at a location distal to the tibial plateau 207 and along the axis of the MCL 97) holes 209 and 211 for receiving screws 81 through the openings 77 and 79, respectively, in the legs 73 and 75, respectively. According to a presently preferred embodiment, the holes 209 and 211 are disposed 10 mm distal to the tibial plateau 207 and on opposite sides of the longitudinal axis of the MCL 97. The template 205 can have holes 213 and 215 for forming the holes 209 and 211. The first attachment structure 25 is fixed to the tibia 27 via the pair of screws 81 through the openings 77 and 79 in the legs and in the holes 209 and 211. The hole 203 may be drilled before or after the holes 213 and 215. The holes 213 and 215 will ordinarily include countersunk portions for receiving the bosses 83 and 85 of the first attachment structure 25. The openings 77 and 79 include an enlarged portion for receiving the heads 91 of the screws 81 so that they do not extend past the outer surface 93 of the first attachment structure.

As seen in FIG. 11B, first end of the laterally and, ordinarily, longitudinally flexible force absorber assembly 33 is attached to a first connection point 71 of the first attachment structure 25. More particularly, a part of the first portion 45 (FIGS. 7A-7D) of the cylinder body 35 is received in the opening 99 (FIGS. 2A-2B) in the first attachment structure 25 and, ordinarily, locked in position so that it is neither axially removable from the opening nor rotatable relative to the opening. The second portion 41 (FIGS. 6A-6B) of the piston 37 (FIG. 4) can be at least partially disposed in the cylinder opening 43.

The remaining portion of the second attachment structure 29 is positioned on the post 103 (FIG. 4)(not visible in FIG. 11B) so that remaining portion of the second attachment structure, primarily the socket 69 and leg 109 of the second attachment structure, are rotatable about the post. This can be done by providing the opening 111 in the remaining portion of the second attachment structure 29 for the post that is of sufficient size to receive the post and permit rotation of the remaining portion of the second attachment member relative to the post.

As seen in FIG. 11C, the remaining portion of the second attachment structure 29 is rotated about the post 103 (not visible in FIG. 11C) to align a second connection point 101 of the second attachment member, ordinarily the socket 69 (FIGS. 3A-3C), with a second end of the force absorber assembly 33, i.e., ordinarily the ball 63 (FIGS. 5A-5C) which is received in the socket. The remaining portion of the second attachment structure 29 can be rotated so that alignment indicia 107 on the second attachment structure aligns with the longitudinal axis of the force absorber assembly 33.

After rotating the remaining portion of the second attachment structure 29 about the post axis 103, the remaining portion of the second attachment structure is fixed to the femur 31 via a screw 81. The opening 105 (FIGS. 3A-3C) for the screw 81 in the leg 109 of the second attachment structure 29 can function as a template for drilling a hole 217 for the screw in the femur 31.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed is:

1. An implantable assembly for a knee joint, comprising:
a first attachment structure configured to be attached to a first member of the knee joint;
a second attachment structure configured to be attached to a second member of the knee joint; and
a force absorber assembly connected to the first attachment structure and the second attachment structure, the absorber assembly including a cylinder body connected to the first attachment structure and a piston connected to the second attachment structure, the piston including a first portion connected to the second attachment structure and a second portion receivable in a cylinder body opening of the cylinder body, the second portion of the piston being of greater flexibility than the first portion of the piston;
wherein the first attachment structure comprises a connection point for the cylinder body and a pair of legs disposed on opposite sides of the connection point, each leg comprising an opening for receiving a screw;
wherein the pair of legs define an obtuse angle relative to each other; and
wherein the pair of legs define, with a tibia to which they are to be mounted, a space of sufficient size to span a medial collateral ligament.

2. The implantable assembly as set forth in claim 1, wherein the cylinder body comprises a first portion connected to the first attachment structure and a second portion including at least part of the cylinder body opening in which the second portion of the piston is receivable, the second portion of the cylinder body being of greater flexibility than the first portion of the piston.

3. The implantable assembly as set forth in claim 2, wherein the second portion of the cylinder body is of greater flexibility than the first portion of the cylinder body.

4. The implantable assembly as set forth in claim 2, wherein the first portion of the cylinder body is non-rotatably attached to the first attachment structure.

5. The implantable assembly as set forth in claim 2, wherein the first attachment structure comprises an opening in which an end of the first portion of the cylinder body is locked so that it cannot be removed from the opening.

6. The implantable assembly as set forth in claim 2, wherein the first portion of the cylinder body is disposed at a first end of the second portion of the cylinder body, and the cylinder body comprises a third portion disposed at a second, opposite end of the second portion of the cylinder body, the second portion of the cylinder body being of greater flexibility than the third portion of the cylinder body, the second portion of the piston being adapted to extend through a first portion of the cylinder opening in the third portion of the cylinder body into a second portion of the cylinder opening in the second portion of the cylinder body.

7. The implantable assembly as set forth in claim 6, wherein the first portion of the piston includes a flange portion having a larger diameter than the second portion of the piston and the cylinder opening.

8. The implantable assembly as set forth in claim 7, wherein the second portion of the piston is of greater flexibility than the flange portion.

9. The implantable assembly as set forth in claim 7, wherein the first portion of the piston includes a ball attached to the flange portion.

10. The implantable assembly as set forth in claim 9, wherein the second portion of the piston is of greater flexibility than the ball.

11. The implantable assembly as set forth in claim 10, wherein the second attachment structure comprises a socket in which the ball is received, the force absorber assembly being pivotable relative to the second attachment structure via the ball and socket.

12. The implantable assembly as set forth in claim 1, wherein each leg comprises a boss protruding from a rear surface of the first attachment structure, the opening extending through the boss.

13. The implantable assembly as set forth in claim 12, wherein each boss includes an external surface including one or more axially extending ridges.

14. The implantable assembly as set forth in claim 1, wherein each opening is countersunk in a respective leg to receive an enlarged head portion of the screw beneath an outer surface of the respective leg.

15. The implantable assembly as set forth in claim 1, wherein the space is of sufficient size to permit medial collateral ligament movement.

16. The implantable assembly as set forth in claim 1, wherein the connection point for the cylinder body comprises an opening in the first attachment structure in which a first portion of the cylinder body is locked so that it cannot be removed from the opening.

17. The implantable assembly as set forth in claim 16, wherein the opening of the connection point for the cylinder body comprises an axis that is substantially perpendicular to axes of the screw receiving openings.

18. The implantable assembly as set forth in claim 1, wherein the second attachment structure comprises a connection point for the piston, a post, and an opening for receiving a screw.

19. The implantable assembly as set forth in claim 18, wherein the connection point for the piston comprises a socket in which a ball on the piston is received.

20. The implantable assembly as set forth in claim 19, wherein the force absorber assembly is pivotable relative to the second attachment structure via the ball and socket.

21. The implantable assembly as set forth in claim 19, wherein a longitudinal axis of the post extends through a center of the ball and socket.

22. The implantable assembly as set forth in claim 19, wherein the socket comprises alignment indicia arranged to align with a longitudinal axis of force absorber assembly.

23. The implantable assembly as set forth in claim 18, wherein the second attachment structure comprises a leg extending from the connection point for the piston, the opening for receiving the screw being disposed in the leg.

24. The implantable assembly as set forth in claim 23, wherein the second attachment structure comprises an opening in which the post is received.

25. The implantable assembly as set forth in claim 24, wherein the connection point for the piston comprises a socket in which a ball on the piston is received and a longitudinal axis of the opening for the post extends through a center of the ball and socket.

26. The implantable assembly as set forth in claim 24, wherein a longitudinal axis of the opening for the post defines an acute angle with a longitudinal axis of the opening for the screw.

27. The implantable assembly as set forth in claim 18, wherein a longitudinal axis of the post defines an acute angle with a longitudinal axis of the opening for the screw.

28. The implantable assembly as set forth in claim 1, wherein, when the second portion of the piston is received in the cylinder opening, the piston and the cylinder body are axially rotatable relative to each other.

29. A method for mounting an implantable assembly for a knee joint, comprising:
   fixing a first attachment structure to a tibia via a pair of screws;
   attaching a first end of a laterally and longitudinally flexible force absorber assembly including a cylinder body to a first connection point of the first attachment structure;
   drilling a first hole in a femur;
   inserting a post of a second attachment structure into the first hole; rotating the second attachment structure about the axis of the post to align a second connection point of the second attachment member with a second end of the force absorber assembly; and
   fixing the remaining portion of the second attachment structure to the femur via a screw;
   wherein the first attachment structure comprises a connection point for the cylinder body and a pair of legs disposed on opposite sides of the connection point, each leg comprising an opening for receiving a screw;
   wherein the pair of legs define an obtuse angle relative to each other; and
   wherein the pair of legs define, with a tibia to which they are to be mounted, a space of sufficient size to span a medial collateral ligament.

* * * * *